United States Patent [19]

Vance, Sr. et al.

[11] Patent Number: 5,044,948
[45] Date of Patent: Sep. 3, 1991

[54] SEARCHER

[76] Inventors: Wilbur Vance, Sr., 5634 Arch St., Philadelphia, Pa. 19139; George Spector, 233 Broadway, New York, N.Y. 10007

[21] Appl. No.: 519,766
[22] Filed: May 7, 1990
[51] Int. Cl.⁵ .................................... A61C 1/00
[52] U.S. Cl. ......................... 433/31; 132/309; 15/167.1
[58] Field of Search ............. 132/309; 433/30, 31; 15/167.1

[56] References Cited

U.S. PATENT DOCUMENTS

| 1,473,357 | 11/1923 | Pletman | 132/309 |
| 1,604,873 | 10/1926 | Barnhart | 132/309 |
| 1,616,104 | 2/1927 | Bardera | 132/309 |
| 1,695,451 | 12/1928 | Campbell | 132/309 |

FOREIGN PATENT DOCUMENTS 430270  6/1935  United Kingdom ............... 132/309

Primary Examiner—Robert P. Swiatek
Assistant Examiner—Nicholas D. Lucchesi

[57] ABSTRACT

An improved toothbrush is provided and consists of a mirror assembly adjustably disposed to the distal end of an elongated handle so that a person using the toothbrush may observe the condition of the teeth and mouth.

2 Claims, 1 Drawing Sheet

SEARCHER

BACKGROUND OF THE INVENTION

The instant invention relates generally to toilet accessories and more specifically it relates to an improved toothbrush.

Numerous toilet accessories have been provided in prior art that are adapted to be used for oral hygienic purposes such as inspecting the teeth and keeping them clean. For example, U.S. Pat. Nos. 828,393 to Emerson; 1,604,873 to Barnhaut and 1,620,330 to Douglass all are illustrative of such prior art. While these units may be suitable for the particular purpose to which they address, they would not be as suitable for the purposes of the present invention as heretofore described.

SUMMARY OF THE INVENTION

A primary object of the present invention is to provide an improved toothbrush that will overcome the shortcomings of the prior art devices.

Another object is to provide an improved toothbrush in which a mirror assembly is adjustably attached to the toothbrush handle so that a person may observe the condition of the teeth and mouth.

An additional object is to provide an improved toothbrush in which the mirror assembly can slide within and be withdrawn from the toothbrush handle.

A further object is to provide an improved toothbrush that is simple and easy to use.

A still further object is to provide an improved toothbrush that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE PREFERRED EMBODIMENTS

Figure 1:
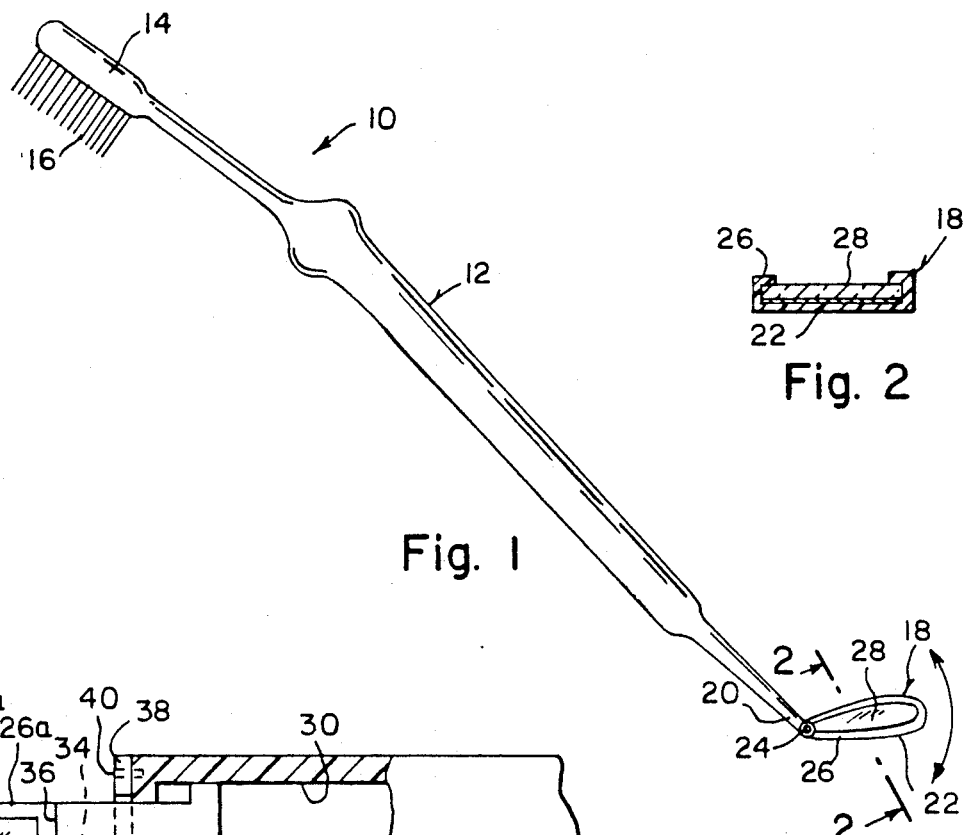
FIG. 1 is a perspective view of the invention.

Turning now descriptively to the drawings, in which similar reference characters denote similar elements throughout the several views, FIG. 1 illustrates an improved toothbrush 10 containing an elongated handle 12 having a head 14 at one end thereof. A plurality of bristles 16 extend from the head 14 for brushing the teeth. A mirror assembly 18 is adjustably disposed to distal end 20 of the handle 12 remote from the head 14 so that a person using the toothbrush 10 may observe the condition of the teeth and mouth.

Figure 2:
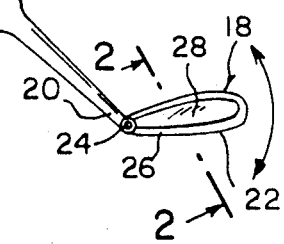
FIG. 2 is a cross sectional view taken along line 2—2 in FIG. 1.

As shown in FIGS. 1 and 2, the mirror assembly 18 includes a backing plate 22 which is pivoted at one side 24 to the distal end 20 of the handle 12. A retaining rim 26 is formed about the periphery of the backing plate 22. A mirror 28 is carried upon the backing plate 22 and held in position by the retaining rim 26.

Figure 3:
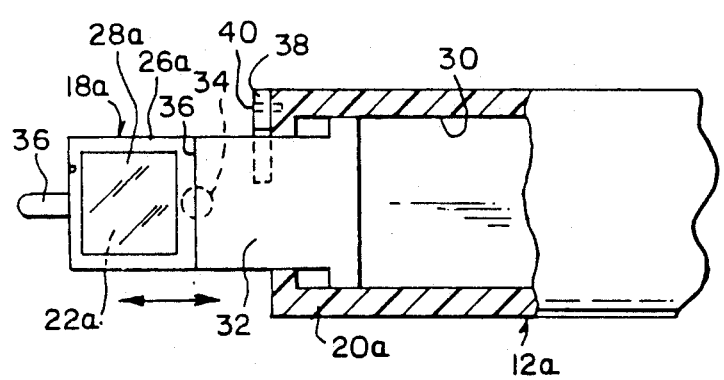
FIG. 3 is an enlarged top view with parts broken away and in section of a modification in which an adjustable mirror is slideable within the toothbrush handle for storage and can be withdrawn for use in viewing ones teeth.
Figure 4:
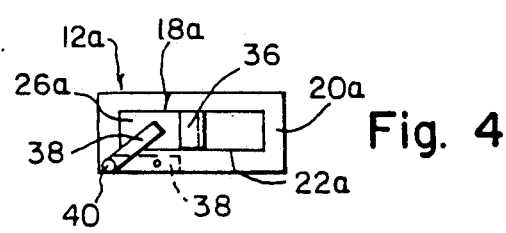
FIG. 4 is an end view of FIG. 3 showing the stop member retaining the mirror in a closed position within the brush handle.

As shown in FIGS. 3 and 4, an alternate mirror assembly 18a is provided and includes the handle 12a having a longitudinal track 30 extending inwardly from the distal end 20a. A slide member 32 rides within the longitudinal track 30, while a ball and socket 34 is carried on free end 36 of the slide member 32. A backing plate 22a is connected to the ball and socket 34 at one side 36 so the backing plate 22a can be angularly adjusted thereto. A retaining rim 26a is formed about periphery of the backing plate 22a. A mirror 28a is carried upon the backing plate 22a and held in position by the retaining rim 26a.

A finger grip 36 extends outwardly from the backing plate 22a opposite the ball and socket 34 so that the mirror assembly 18a can slide within the handle 12a for storage and can be withdrawn for use in viewing the teeth and mouth.

A stop member 38 is pivotable at 40 on distal end 20a of the handle 12a to retain the mirror assembly 18a within the handle 12a for storage.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An improved toothbrush comprising:
   a) an elongated handle having a head at one end thereof;
   b) a plurality of bristles extending from said head for brushing the teeth; and
   c) a mirror assembly adjustably disposed to the distal end of said handle remote from said head so that a person using said toothbrush may observe the condition of the teeth and mouth; wherein said mirror assembly includes:
   d) a slide member with a backing plate pivoted at one side to a distal end of said slide member;
   e) a retaining rim formed about the periphery of said backing plate and fitting inside said distal end of said handle; and
   f) a mirror carried upon said backing plate and held in position by said retaining rim, wherein said mirror assembly further includes:
   g) said handle having a longitudinal track extending inwardly from its distal end;
   h) said slide member rides within said longitudinal track;
   i) a ball and socket carried on a free end of said slide member;
   j) said backing plate is connected to said ball and socket at one side so said backing plate can be angularly adjusted about an axis longitudinal of said handle;
   k) a finger grip extending outwardly from said backing plate opposite said ball and socket so that said mirror assembly can slide within said handle for storage and can be withdrawn for use in viewing the teeth and mouth.

2. An improved toothbrush as recited in claim 1, further comprising a stop member pivotable on the distal end of said handle to engage said rim to retain said mirror assembly within said handle for storage.

* * * * *